United States Patent [19]

Drouin et al.

[11] 4,294,015
[45] Oct. 13, 1981

[54] EXTENSOMETER

[75] Inventors: Gilbert Drouin, L'Acadie; Jacques Sibille, Beloeil, both of Canada

[73] Assignee: Ecole Polytechnique, Quebec, Canada

[21] Appl. No.: 107,574

[22] Filed: Dec. 27, 1979

[51] Int. Cl.³ .............................................. G01B 7/16
[52] U.S. Cl. ................................ 33/174 D; 33/148 D; 33/149 J; 33/DIG. 13; 33/143 L; 128/774; 128/782; 73/767
[58] Field of Search ............ 33/174 D, 143 C, 143 L, 33/147 D, 148 D, 149 J, DIG. 13; 128/774, 782; 73/767, 776

[56] References Cited

U.S. PATENT DOCUMENTS

| 2,543,429 | 2/1951 | Wood | 33/148 D |
| 2,666,262 | 1/1954 | Ruge | 33/143 L |
| 2,744,181 | 5/1956 | Rea | 33/143 L |
| 2,917,920 | 12/1959 | Robinette, Jr. et al. | 33/147 D |
| 4,141,345 | 2/1979 | Allen et al. | 33/149 J |

Primary Examiner—Willis Little
Attorney, Agent, or Firm—Oblon, Fisher, Spivak, McClelland & Maier

[57] ABSTRACT

An extensometer for detecting traumatized ligaments where the elongation of the ligament is either abnormally large or abnormally small compared to the elongation measured on a healthy ligament for an angle of flexion of the knee. The extensometer includes at least one flexible member having a strain gauge secured thereto to measure deflexion of the flexible member from its normal configuration. The flexible member has a free end and is secured at its opposed end to a support base. A clamping member is provided to retain the free end of the flexible member on a ligament while maintaining the support base substantially stationary with respect to the ligament whereby elongation of the ligament is detected by the deformation of the flexible member from its initial configuration.

9 Claims, 8 Drawing Figures

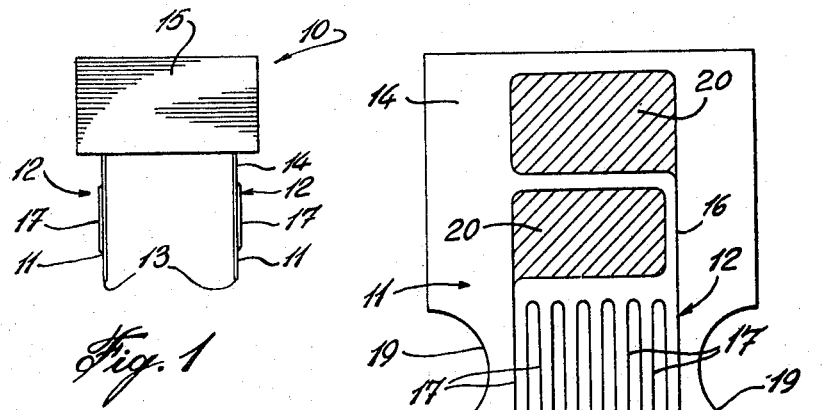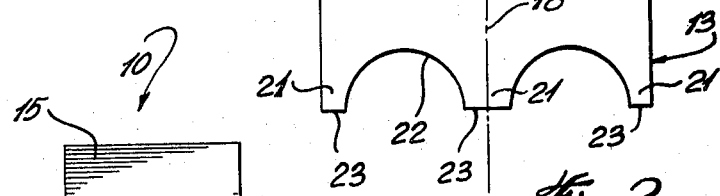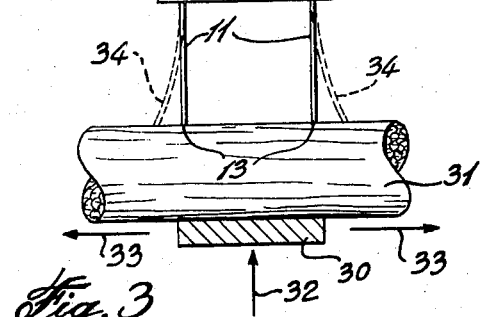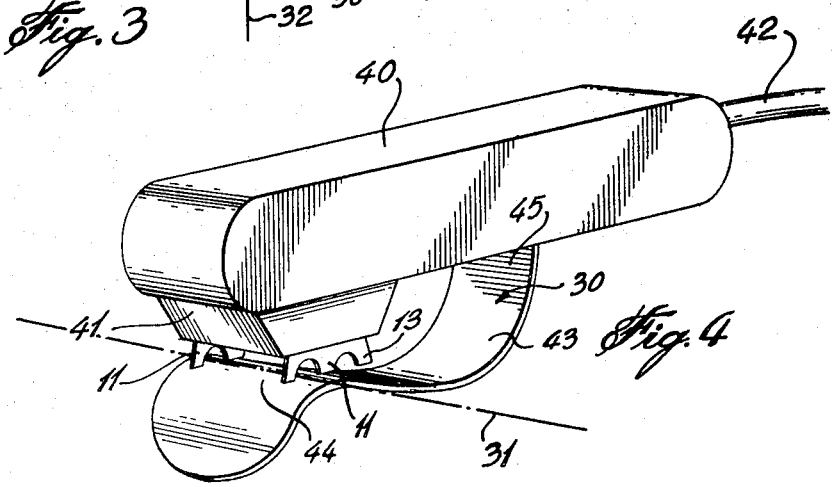

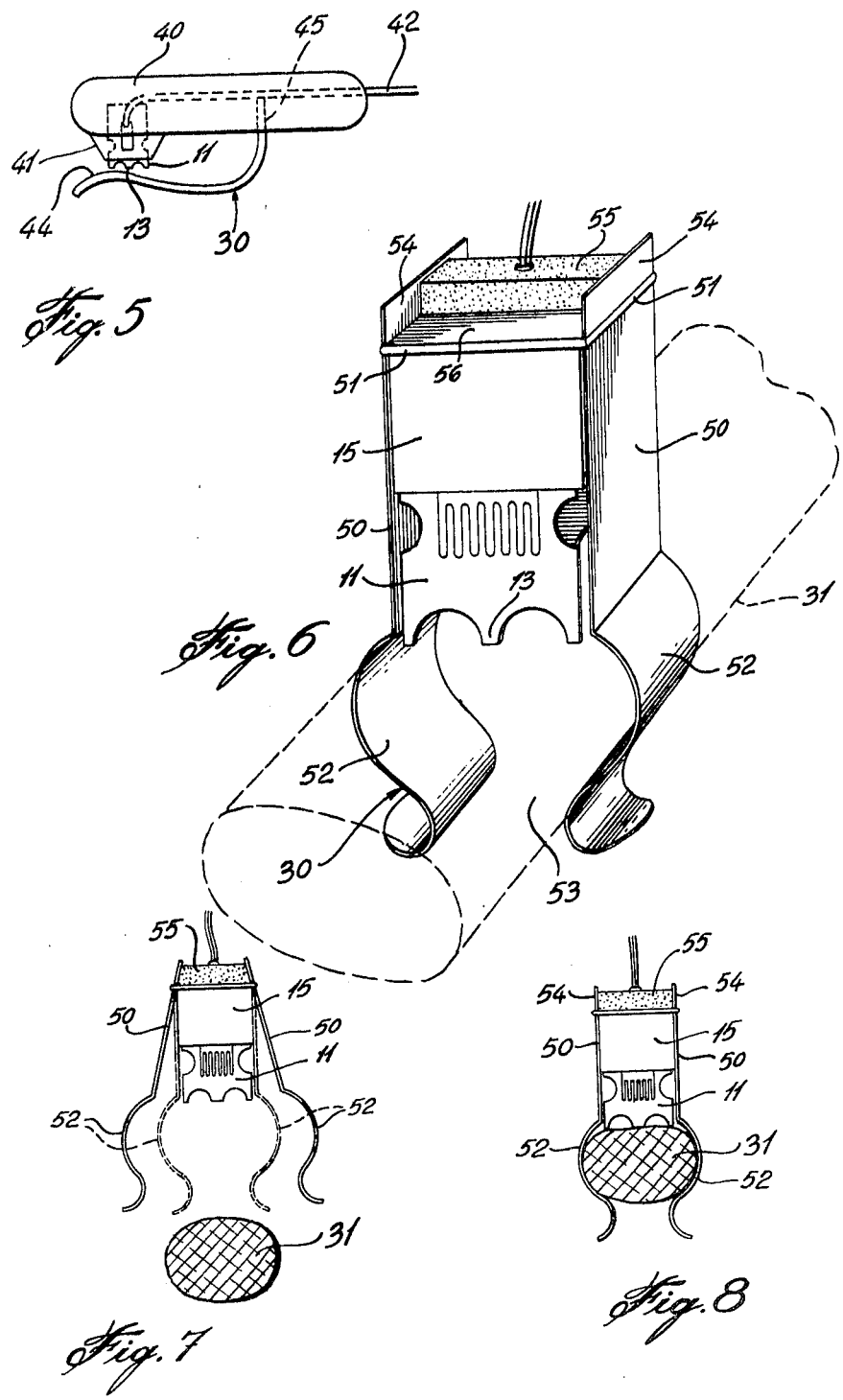

EXTENSOMETER

BACKGROUND OF THE INVENTION

1. Field of the Invention

The present invention relates to an extensometer for detecting traumatized ligaments.

2. Description of the Prior Art

The present techniques utilized to detect traumatized ligaments are imprecise and require open knee surgery to visually inspect the ligaments to determine if it is traumatized, that is to say, if the ligament has been ruptured, elongated, etc. Of the apparatus known to measure deformation, these are too large to be utilized in measuring ligaments of the knee and a large number of these apparatus are not precise enough to make a proper measurement. Other known apparatus are so constructed that their probes would damage the ligament if they were to attempt to use such apparatus on ligaments. Thus, with the deficiency in diagnostic apparatus for detecting traumatized ligaments, the technique utilized today by physicians is not precise and is often inadequate.

SUMMARY OF THE INVENTION

It is a feature of the present invention to provide an extensometer for detecting traumatized ligaments which substantially overcomes all of the abovementioned disadvantages.

It is a further feature of the present invention to provide an extensometer for detecting traumatized ligaments which measures the elongation in ligaments when the ligaments are stretched, which stretching is effected by flexing the knee in the case of knee ligaments.

A further feature of the present invention is to provide an extensometer which will give a precise measure of the elongation of the ligament between two given points.

A further feature of the present invention is to provide a method of detecting traumatized ligaments by means of an extensometer which will measure the elongation of a ligament when stretched.

Another feature of the present invention is to provide a method of detecting traumatized ligaments by means of an extensometer of a miniaturized type that may be used with an arthroscope.

According to the above features, from a broad aspect, the present invention provides an extensometer for detecting deformation of elongatable members. The extensometer includes at least one flexible member having a strain gauge secured thereto to measure deflexion of the flexible member from its normal configuration. The flexible member has a free end and is secured at is opposed end to a support base. A clamping assembly is provided for retaining the free end of the flexible member on an elongatable member whilst maintaining the support base substantially stationary with respect to the elongatable member whereby elongation of the elongatably member is detected by flexion of the flexible member from its normal configuration.

According to a further broad aspect of the present invention, there is provided a method of detecting elongation of elongatable members. The method includes the steps of providing at least one flexible member having a strain gauge thereon, a free end and an opposed end secured to a support base. The free end of the flexible member is clamped on an elongatable member and the support base is retained substantially stationary with respect to the elongatable member. The elongatable member is then stretched axially and the elongation thereof is detected by the deflexion of the flexible member from its initial configuration.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts through the several views and wherein:

FIG. 1 is a side view of the extensometer of the present invention;

FIG. 2 is a side view of a flexible member of the extensometer showing the strain gauge;

FIG. 3 is a side view of the extensometer showing its operation in measuring elongation in a stretched ligament;

FIG. 4 is a perspective view of an extensometer designed in accordance with the invention;

FIG. 5 is a side view of FIG. 4;

FIG. 6 is a perspective view of a further design of the extensometer of the invention; and FIGS. 7 and 8 are side views showing the manner in which a ligament is clamped against the flexible plates of the extensometer.

DETAILED DESCRIPTION OF THE PREFERRED EMBODIMENTS

Referring now to the drawings, and more particularly to FIGS. 1 to 3, there is shown generally at 10, the extensometer of the present invention. The extensometer includes essentially two flexible plates or members 11 each having a strain gauge 12 secured thereto. The flexible plate 11 has a free end 13, for engagement with an elongatable member to detect elongation thereof. The other or opposed end is a securable end 14 secured within a support base 15.

Referring more specifically to FIG. 2, there is shown the construction of the strain gauge 12 (well-known in the art) and it consists of a fine wire 16 disposed in a serpentine path consisting of side-by-side parallel rows of wire with the longitudinal axis of each path 17 extending co-axially with the axis of flexion or the longitudinal axis 18 of the plate 11. As herein shown, the flexible plates are designed to adapt to ligaments and are formed with a narrow area in the area of the serpentine path of the wire by cut-outs 19 in opposed longitudinal edges of the plate 11. The cut-outs 19 make the plate more flexible in the strain gauge area. The ends of the wire 16 terminate in terminals 20 for connection to suitable measuring apparatus or to electronic circuit member (not shown) which provide an output signal representative of a change in resistance in the wire 16 by the flexion of the plate.

The free end 13 of each plate 11 terminates in a gripping mechanism which is herein constituted by teeth-like protrusions 21 formed by the cut-outs 22 in the lower edge of the plate 11. These teeth-like protrusions permit better gripping with the ligament and are terminated in blunt ends 23 to prevent damaging the ligament surface. The flexible plates 11 are very thin plates of miniature size. Of course, the free end 13 may have a different configuration to achieve the same results.

FIG. 3 illustrates the operation of the extensometer 10 and, as shown, clamping member 30, as will be described in detail later with respect to the embodiments of FIGS. 4 and 6, retain the free ends 13 of both flexible plates 11 against one side of a ligament 31 by applying a force F in the direction of arrow 32, thus pushing the ligament transversely against the plates 11. The clamping member 30 also maintains the support base 15 substantially stationary with respect to the ligament 31. When the ligament 31 is stretched from its ends in the directions of arrows 33, the elongation of the ligament 31 is detected by flexion of the flexible members 11, as illustrated by their phantom position 34. This deflexion causes a change in the resistance of the strain gauge wire 16 and this is measured by electronic circuit member, and in this case, by connecting the strain gauge in a Wheatstone bridge circuit (not shown) to give a signal representative of proper functioning of the ligament. It can be seen that if the ligament was severed, the force applied in the direction of arrows 33 would cause the ligament to move in both directions away from the rupture, that is to say, in both directions of the arrows 33. Depending on the location of the extensometer relative to the rupture, the flexible plates 11 will flex abnormally away from each other if the rupture is between the plates. However, if the extensometer is positioned to one side of the rupture, the deformation of the plates will be negligible as there would be no deformation in that part of the ligament. In the case of a damaged but unsevered ligament, the flexion of the plates 11 would result in an output signal, given by the electronic circuit member, correlated to represent the degree of severity of the injury.

Referring now to FIGS. 4 and 5, there is shown one embodiment of the construction of the extensometer. As herein shown, the device consists of a housing 40 into which the support base 15 is secured and a shield 41 surrounds the flexible plates 11 extending out of the housing 40. The hollow shield member 41 prevents damage to the ligament and permits the proper flexion of the plates 11. A cable 42 connects the strain gauges to a remote electronic circuit member (not shown). The circuit member could also conveniently be mounted in the housing 40.

As shown in FIGS. 4 and 5, the clamping member 30 includes a leaf spring 43 having a clamping portion 44 and a fixed end portion 45 secured within the housing 40. The clamping portion 44 is angulated and disposed adjacent the flexible members 11 to clamp a ligament onto the free end 13 of the flexible members with the pressure being applied transverse to the ligament by the force exerted by the spring 43.

Referring now to FIGS. 6 to 8, there is shown a further embodiment of the extensometer construction. As herein shown, the clamping member 30 is constructed as a caliper clamp including opposed walls 50 hinged at a common end by a hinge connection 51. The walls 50 each are arcuately formed in a lower end to define a ligament receiving end 52 with opposed walls defining a mouth opening 53 between the free ends of the walls 50.

A spring-like member 55 is secured on the top end 56 of the support base 15 and extends between the top end 54 of the walls 50. By pressing the top ends 54 toward one another, the walls 50 will diverge away from one another, as shown in FIG. 7, to open the mouth opening 53 to allow the ligament 31 to be grasped within the mouth and between the ligament receiving portions 52.

By releasing the top end of the opposed walls 50, the walls will come back to their original position by the biasing force of the member 55 against the top ends 54 of the walls 50, and squeeze the ligament 31 against the free end 13 of the flexible plates 11. There is insufficient pressure in the clamp to cause the ligament 31 to elongate when it is stretched between its ends.

Obviously, numerous modifications and variations of the present invention are possible in light of the above teachings. It is therefore to be understood that within the scope of the appended claims, the invention may be practiced otherwise than as specifically described herein. For example, it is conceivable that instead of having two flexible plates, there may be provided a single flexible plate 11 with the support base 15 being retained stationary with respect to the ligament by the clamping means. Also, the flexible member may be a plate or other flexible element having a detection mechanism capable of detecting the flexion thereof. Furthermore, the extensometer of the present invention may be used to measure elongation of other type deformable members or membranes such as to measure skin deformation or to determine the elastomeric properties of tissue or cables constructed of extensible strands.

We claim:

1. An extensometer for detecting deformation of a biological elongatable member to be stretched, said extensometer comprising:
   a support base;
   a pair of spaced-apart flexible plates;
   a strain gauge secured to each of said flexible plates for measuring deflection of said flexible plates, from the normal plane of said flexible plates;
   said flexible plates each further comprising a free end and an opposed end, said opposed end secured to said support base;
   said free end further comprising gripping means for engagement in a surface portion of said elongatable member; and
   clamping means for applying a force perpendicular to said elongatable member positioned opposite said gripping means of said pair of flexible plates to cause said gripping means to positively engage in said surface portion of said elongatable member, said clamping means being secured to said support base for maintaining said support base substantially stationary with respect to said elongatable member such that elongation of said elongatable member is detected by flexion of said flexible plates.

2. An extensometer as claimed in claim 1 wherein said biological elongatable member comprises a ligament.

3. An extensometer as claimed in claim 2 wherein said flexible plates comprise thin plates, said gripping means further comprising teeth-like protrusions formed in said free end of said plates.

4. An extensometer as claimed in claim 1, said flexible plates having at least one cut out portion formed therein in the area of said strain gauge, said strain gauge comprising a wire forming a plurality of adjacent parallel paths with the longitudinal axis of each said paths of said wire extending coaxially with the axis of flexion of each said flexible plates.

5. An extensometer for detecting deformation for elongatable members, said extensometer comprising:
   a support base;
   at least one flexible member;

a strain gauge secured to said flexible member for measuring deflection of said flexible member from the normal configuration of said flexible member;

said flexible member comprising a free end and an opposed end, said opposed end being secured to said support base;

clamping means for retaining said free end of said flexible member on an elongatable member while maintaining said support base substantially stationary with respect to said elongatable member such that elongation of said elongatable member is detected by flexion of said flexible member by the axial displacement thereof, and wherein said elongatable member comprises a ligament;

said at least one flexible member comprising a pair of spaced-apart flexible members; and said clamping means comprising a clamp member adapted to push a portion of said ligament against said free end of said flexible members.

6. An extensometer as claimed in claim 5 wherein said clamp member further comprises a leaf spring having a clamping portion and a fixed end portion, said fixed end portion being immovably secured with respect to said support base, said clamping portion being disposed adjacent said flexible member for clamping said ligament onto said free end of said members such that said ligament is disposed between said members and said clamping portion.

7. An extensometer as claimed in claim 5 said clamp member further comprising a caliper clamp having opposed walls hinged at a common end, an end for receiving said ligament comprising a free end of each said walls wherein each said ligament receiving end is disposed on a respective one of opposed sides of said flexible members below said free end of said members and spaced apart to include a mouth opening, said ligament receiving end being displaceable by said hinged common end to enlarge said mouth opening to restrain said ligament therethrough and transverse to said flexible members such that said elongation may be detected.

8. A method of detecting deformation of a biologically elongatable member utilizing a pair of spaced-apart flexible plates each including a strain gauge thereon, a free end with gripping means for engagement in a surface portion of an elongatable member to be stretched, an opposed end secured to a support base, and a clamping means positioned opposite said gripping means comprising the steps of:

clamping said free end of said flexible plates on said elongatable member with said clamping means by applying a force perpendicular to said elongatable member to cause said gripping means to positively engage said surface portion or said elongatable member, retaining said support base substantially stationary with respect to said elongatable member, stretching said elongatable member axially, and detecting elongation of said elongatable member by deflexion of said flexible plates from the normal plane of said flexible plates.

9. An extensometer as claimed in claim 1 wherein said spaced-apart flexible plates are disposed on one side of said biological elongatable member.

* * * * *